US005374517A

United States Patent [19]
Sculley et al.

[11] Patent Number: 5,374,517
[45] Date of Patent: Dec. 20, 1994

[54] IM PEPTIDES

[75] Inventors: Tom B. Sculley, Nathan; Denis J. Moss, Arana Hills, both of Australia

[73] Assignee: Council of the Queensland Institute of Medical Research, Herston, Australia

[21] Appl. No.: 859,291

[22] PCT Filed: Nov. 23, 1990

[86] PCT No.: PCT/AU90/00564

§ 371 Date: May 22, 1992

§ 102(e) Date: May 22, 1992

[87] PCT Pub. No.: WO91/08224

PCT Pub. Date: Jun. 13, 1991

[30] Foreign Application Priority Data

Nov. 24, 1989 [AU] Australia ............... PJ7584

[51] Int. Cl.$^5$ ............ C07K 7/06; C07K 7/08; C07K 7/10; G01N 33/569
[52] U.S. Cl. ................. 435/5; 435/7.95; 435/975; 436/812; 530/325; 530/326; 530/329
[58] Field of Search ............... 435/5, 7.95, 975; 436/812, 513, 547; 424/86, 89; 530/326, 329, 806, 863, 812, 826, 325, 389.4, 388.3

[56] References Cited

U.S. PATENT DOCUMENTS 4,554,101 11/1985 Hopp ................. 424/89
4,707,358 11/1987 Kieff et al. ............ 424/89

FOREIGN PATENT DOCUMENTS

82073/87 6/1988 Australia .
44000/89 2/1990 Australia .
0316170 5/1989 European Pat. Off. .

OTHER PUBLICATIONS

Middeldorp et al., 1988b. Epitope mapping on the Epstein-Barr virus major capoid protein using systemic synthesis of overlapping oligopeptides. J. Virolog. Meth. 21:147-59.

(List continued on next page.)

Primary Examiner—David Saunders
Assistant Examiner—James L. Grun
Attorney, Agent, or Firm—Larson and Taylor

[57] ABSTRACT

The invention is directed to the diagnosis and treatment of herpes virus related diseases. By noting within the Epstein-Barr virus (EBV) open reading frames (ORFs) transcribed late in the viral cycle for which a translation product may or may not have been established, and synthesizing one or more polypeptides each of which includes at least one segment, each segment comprising at least part of the amino acid sequence identified in that ORF, a specific and reliable diagnostic test for, and treatment of, infectious mononucleosis and related diseases is possible. The preferred amino acid sequences for these segments include NSPKNG (SEQ ID NO: 12), KNGSNQ (SEQ ID NO: 13), SNQLVI (SEQ ID NO: 14), AHARDK (SEQ ID NO: 15), RDKAGA (SEQ ID NO: 16), VMAMIL (SEQ ID NO: 17), SEPRPR (SEQ ID NO: 18), and PSRTPS (SEQ ID NO: 19). These sequences can be further combined to provide polypeptides with at least one segment comprising sequences selected from AHARDKAGAVMAMIL (SEQ ID NO: 1), ASLNSPKNGSNQLVI (SEQ ID NO: 2), ELESEPRPRPSRTPS (SEQ ID NO: 3), QAMKKIEDKVRKSVD (SEQ ID NO: 4), SRSRGREAKKVQISD (SEQ ID NO: 5), LIKASLRKDRKLYAE (SEQ ID NO: 6), VSFSKTRRAIRESRA (SEQ ID NO: 7), CNYSAGEEDDQYHAN (SEQ ID NO: 8), RPHRRPVSKRPTHKP (SEQ ID NO: 9), EITQEENRGEQRLGH (SEQ ID NO: 10), GALRARLDRPRPTAQ (SEQ ID NO: 11), NSPKNGSNQAHARDKSEPRPR (SEQ ID NO: 20), NSPKNGSNQRDKAGASEPRPR (SEQ ID NO: 21), NSPKNGSNQSEPRPRKNGSNQ (SEQ ID NO: 22), NSPKNGSNQLVISEPRPRPSRTPS (SEQ ID NO: 23), NSPKNGSNQLVIPSRTPS (SEQ ID NO: 24), and NSPKNGSNQAHARDKAGASEPRPR (SEQ ID NO: 25).

28 Claims, 2 Drawing Sheets

OTHER PUBLICATIONS

Middeldorp et al., 1988a. Epstein–Barr virus specific marker molecules for early diagnosis of infectious mononucleosis, J. Virolog. Meth., 21:133–46.

Sculley et al., 1986. Reactions of sera from patients with rheumatord arthritis systemic lupus erythematosus and infections mononucleosis to Epstein–Barr Virus-induced Polypeptides, J. Gen. Virol., 67:2253–8.

Sculley et al., 1985. Identification of Epstein–Barr Virus-induced polypeptides in P3HR-1 cells by protein immunoblot. J. Gen. Virol. 66:1113–22.

Baer et al., 1984. DNA sequence and expression of the B95–8 Epstein–Barr virus genome. Nature 310:207–11.

Mackett et al., Jun. 1990, Characterization and expression of a glycoprotein encoded by the Epstein–Barr virus Bam HI I fragment. J. Virol. 64:2545–52.

Seguin et al., 1983. DNA sequence and transcription of the Bam HI fragment B region of B95–8 Epstein–Barr virus. Mol. Biol. Med., 1:369–92.

Parker et al., 1986. New hydrophilicity seale derived from high-performance liquid chromatography peptide retention data: correlation of predicted surface residue with antigenicity and X-ray-derived accessible sites. Biochem. 25:5425–32.

Kinney et al., 1989. The full-length nucleotide sequence of the verulent Trinidad Donkey Strain of Venezualan equine encephalitis virus and its attenuated vaccine derivative, strain TC–83. Virol. 170:19–30.

Walls et al.; "The analysis of EBV proteins which are antigenic in vivo"; Nucleic Acids Research, vol. 16, No. 7, 1988.

IM PEPTIDES

TECHNICAL FIELD

THIS INVENTION is directed to the diagnosis and treatment of herpes virus related diseases. In particular, it relates to the use of specific open reading frames (ORFs) within the Epstein-Barr virus (EBV) which encode antigens recognized by EBV-specific antibodies raised during infectious mononucleosis (IM) and related diseases and the use of synthetic peptides based on the amino acid sequences encoded by these ORFs in a specific and reliable diagnostic test for, and treatment of, IM and related diseases.

BACKGROUND ART

Epstein-Barr virus (EBV) is a member of the herpes virus family and is present in all human populations. Primary infection usually occurs in early childhood and remains silent throughout a person's life. However, when uninfected adolescents and young adults are exposed to EBV, about 60% manifest infectious mononucleosis (IM).

The predominant laboratory test used to establish the diagnosis of IM has been the demonstration of heterophil antibodies. The rapid slide tests have become the most widely used method to detect these heterophil antibodies. In contrast, quantitative agglutination tests, such as the Paul-Bunnell-Davidsohn method, are more accurate but are also more tedious and time consuming.

The use of tests to measure heterophil antibodies have limitations, namely, only between 80–95% of IM patients produce these antibodies, these antibodies are absent in a large percentage of young children and the antibodies are produced in a variety of other diseases such as lymphoma, hepatitis and leukemia. The measurement of heterophil antibodies also does not give any indication of the severity of the disease and cannot be used to monitor the course of IM.

Immunofluoresence tests that measure antibodies to EBV can also be used in the diagnosis of heterophil-negative cases of IM, or patients with atypical manifestations.

These tests, however, are time consuming and require the use of trained personnel and specialized equipment which does not make them amenable to the routine analysis of large numbers of samples.

The diagnosis of an acute primary EBV infection can also be determined by an IgM response to EBV-viral capsid antigen (VCA). The VCA is composed of a large number of different antigens. Components of VCA are defined by the fact that they are expressed late in the replicative cycle of the virus. Many VCA components have been mapped to specific open reading frames (ORF's) within the EBV genome though there are many ORF's, known to be expressed late in replication, to which specific VCA antigens have not yet been identified.

Genetic engineering and synthetic polypeptide technologies now enable the manufacture of large quantities of protein and polypeptide antigens. However, these techniques are only effective if the amino acid residue sequence of the native protein is known.

The amino acid residue sequence of a natural protein can be determined by sequencing of the protein itself. Alternatively, the DNA sequence that codes for the protein may also reveal the protein's amino acid residue sequence.

Antibodies can be used to determine whether an ORF present in a DNA sequence codes for a protein. This involves manufacturing an array of protein fragments or synthetic polypeptides whose amino acid residue sequences correspond to the hypothetical sequences obtained from the ORFs. The protein fragments or polypeptides to which naturally occurring antibodies immunoreact thereby identify the ORF as encoding a naturally occurring protein. The complete amino acid sequence of this protein could then be deduced from the DNA sequence of the ORF.

DISCLOSURE OF THE INVENTION

It is a general object of the present invention overcome, or at least ameliorate, one or more of the above disadvantages, and to provide a specific and reliable test for the diagnosis for, and treatment of, IM and related diseases.

As the complete DNA sequence for EBV has been identified, including the start and stop codons which, prima facie, define potential ORFs for the transcription of the genetic code, the present inventors have synthesized peptides based on the predicted amino acid sequences encoded by these ORFs, even though the proteins to which these ORFs may relate were not first established as being produced by the virus, and have demonstrated that EBV-specific antibodies raised during IM react with the synthesized peptides.

Thus, according to a first aspect of the present invention, there is provided a peptide comprising a sequence which includes at least one segment which codes for an antigen recognized by EBV-specific antibodies raised during IM or a related disease.

As a second aspect, the present invention also includes within its scope a method of identifying a polypeptide suitable for use in the diagnosis of IM and related diseases, said method comprising:

(1) noting within EBV open reading frames transcribed late in the viral cycle for which a translation product may or may not have been established;

(2) synthesising one or more polypeptides each of which includes at least one segment wherein each segment comprises at least part of the amino acid sequence identified in that open reading frame; and (3) determining whether said polypeptide is effective in the diagnosis of IM and related diseases.

When sera from patients who exhibited clinical symptoms of IM and related diseases were assayed using the peptides of the invention, a positive reaction was noted with a high correlation between this assay and known assays for identifying IM and related diseases.

Therefore, according to a third aspect of the present invention, there is provided a method of diagnosis of infectious mononucleosis or a related disease, said method comprising assaying serum from a patient suspected of having infectious mononucleosis or a related disease with at least one peptide as hereinbefore defined.

The present invention also provides, as a fourth aspect, a kit for use in the diagnosis of IM or a related disease, said kit comprising:

(a) at least one peptide as hereinbefore defined; and (b) a means for indicating the presence of a reaction, particularly an immunoreaction, between said at least one peptide and another molecule(s), especially anti-EBV antibodies.

Since a patient with IM or a related disease contains antibodies to the peptides of the invention, it is likely that the peptides of the invention, when administered to the patient, would elicit anti-EBV antibodies.

Therefore, as a fifth aspect of the present invention, there is provided a vaccine that, when administered, is capable of inducing antibodies effective against EBV, said vaccine comprising:
(a) at least one peptide as hereinbefore defined; and
(b) a carrier and/or diluent and/or adjuvant.

As used throughout the specification, the term "carrier or diluent" denotes an organic or inorganic, natural or synthetic material with Which the active ingredient is combined in order to facilitate the administration of the vaccine of the invention. This carrier or diluent is, therefore, generally inert and it must be pharmaceutically acceptable. Similarly, the term "adjuvant" has the usual meaning in the art to describe a material which aids the operation of the active ingredient.

According to a sixth aspect of the present invention, there are also provided antibodies and substantially whole antibodies raised to—or induced by—the peptides of the invention as hereinbefore defined.

These molecules are collectively referred to as receptors and can be raised in animal hosts using the vaccine as hereinbefore defined.

Preferably, the peptide of the invention comprises at least one segment selected from the following sequences:

| | |
|---|---|
| AHARDKAGAVMAMIL | (SEQ ID NO: 1) |
| ASLNSPKNGSNQLVI | (SEQ ID NO: 2) |
| ELESEPRPRPSRTPS | (SEQ ID NO: 3) |
| QAMKKIEDKVRKSVD | (SEQ ID NO: 4) |
| SRSRGREAKKVQISD | (SEQ ID NO: 5) |
| LIKASLRKDRKLYAE | (SEQ ID NO: 6) |
| VSFSKTRRAIRESRA | (SEQ ID NO: 7) |
| CNYSAGEEDDQYHAN | (SEQ ID NO: 8) |
| RPHRRPVSKRPTHKP | (SEQ ID NO: 9) |
| EITQEENRGEQRLGH | (SEQ ID NO: 10) |
| GALRARLDRPRPTAQ | (SEQ ID NO: 11) |

More preferably, the peptide of the invention comprises at least one segment selected from the following sequences:

| | |
|---|---|
| NSPKNG | (SEQ ID NO: 12) |
| KNGSNQ | (SEQ ID NO: 13) |
| SNQLVI | (SEQ ID NO: 14) |
| AHARDK | (SEQ ID NO: 15) |
| RDKAGA | (SEQ ID NO: 16) |
| VMAMIL | (SEQ ID NO: 17) |
| SEPRPR | (SEQ ID NO: 18) |
| PSRTPS | (SEQ ID NO: 19) |

Most preferably, the peptide of the invention comprises at least one segment selected from the following sequences:

| | |
|---|---|
| NSPKNGSNQAHARDKSEPRPR | (SEQ ID NO: 20) |
| NSPKNGSNQRDKAGASEPRPR | (SEQ ID NO: 21) |
| NSPKNGSNQSEPRPRKNGSNQ | (SEQ ID NO: 22) |
| NSPKNGSNQLVISEPRPRSRTPS | (SEQ ID NO: 23) |
| NSPKNGSNQLVIPSRTPS | (SEQ ID NO: 24) |
| NSPKNGSNQAHARDKAGASEPRPR | (SEQ ID NO: 25) |

A particularly preferred peptide of the invention comprises at least one segment containing the sequence:

| | |
|---|---|
| NSPKNGSNQLVIPSRTPS | (SEQ ID NO: 24) |

All amino acid residues identified throughout the specification are in the natural or L-configuration. In keeping with standard polypeptide nomenclature abbreviations for amino acid residues are as follows:

| SYMBOL | AMINO ACID |
|---|---|
| Y | L-tyrosine |
| G | glycine |
| F | L-phenylalanine |
| M | L-methionine |
| A | L-alanine |
| S | L-serine |
| I | L-isoleucine |
| L | L-leucine |
| T | L-threonine |
| V | L-valine |
| P | L-proline |
| K | L-lysine |
| H | L-histidine |
| Q | L-glutamine |
| E | L-glutamic acid |
| W | L-tryptophan |
| R | L-arginine |
| D | L-aspartic acid |
| N | L-asparagine |
| C | L-cysteine |

BRIEF DESCRIPTION OF THE DRAWING FIGURES

DETAILED DESCRIPTION OF EMBODIMENTS

Subjects, Materials and Methods

Preparation And Use Of Synthetic Peptides

Figure 1:
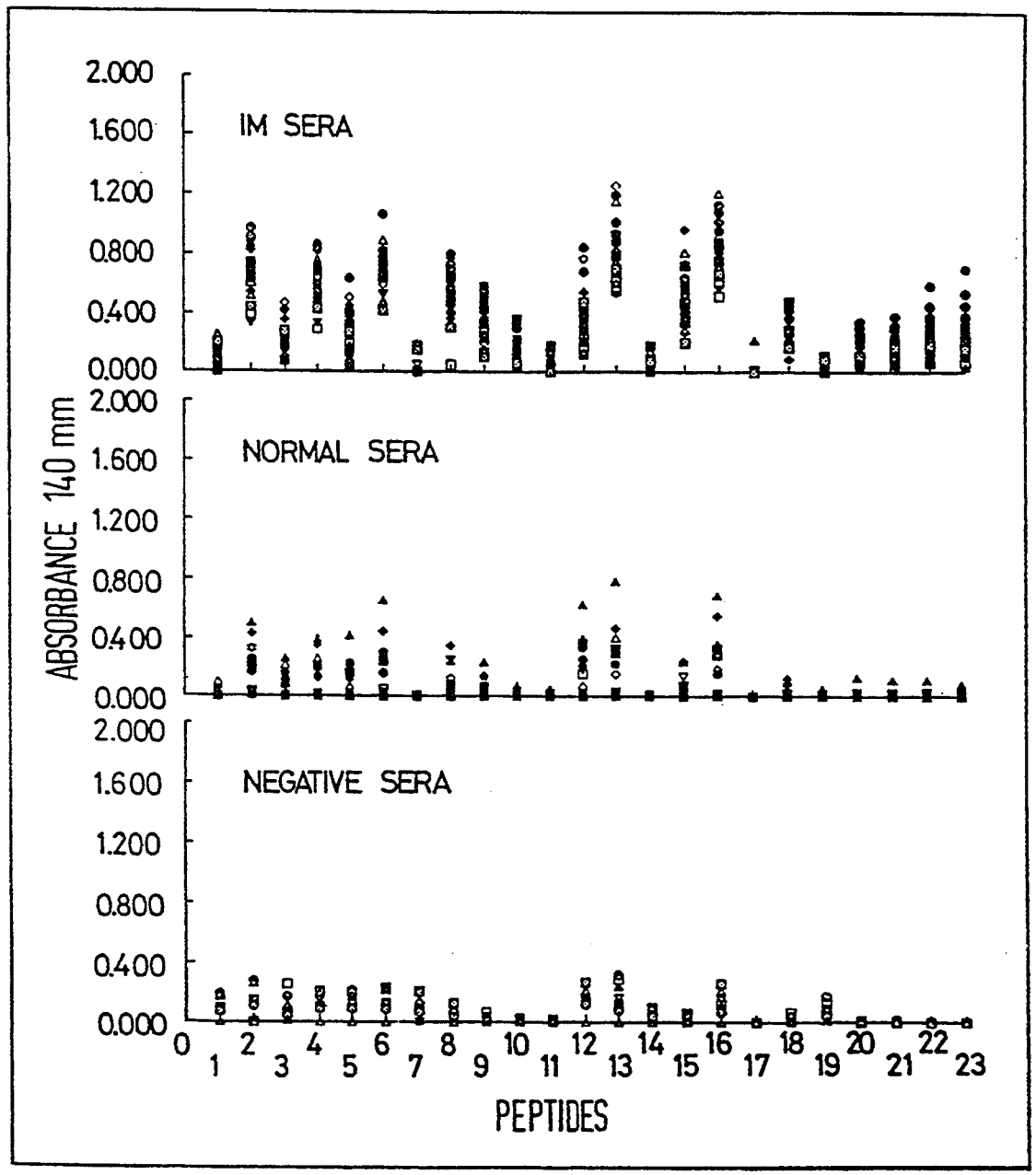
FIG. 1 is a graphic representation of the data from screening the peptides of the invention against samples of sera from confirmed IM patients.

Peptides (15 aa each) were synthesized by the Multiple Simultaneous Peptide technique (MSPS) of Houghton, R. A. (1985, Proc. Natl. Acad. Sci. USA 82, 5131–5135). The synthetic peptides were linked to bovine serum albumin (BSA) with glutaraldehyde as described by Bulinski et al. (1983, Proc. Natl. Acad. Sci. USA 80, 1506–1510). Essentially, 5 mg of dry peptide were added to 0.5 ml (4 mg/ml) BSA in 100 mM phosphate buffer, pH 7.3. To this were added 0.25 ml of 0.25% (v/v) glutaraldehyde for each mg of dry peptide. The solution was left in the dark over night at 21° C. to conjugate, after which the solution was extensively dialyzed against PBS containing 50 mM glycine, pH 7.3. The conjugated peptides were then stored at −20° C. until needed. Peptide sequences, deduced from 13 different ORFs transcribed late in viral replication, were synthesized. These peptides are identified in Table 1.

TABLE 1
VCA PEPTIDES

| ORF | PEPTIDES | | NUMBER |
|---|---|---|---|
| BCRF1 | AENQDPEAKDHVNSL | (SEQ ID NO: 26) | 1 |
| BCRF1 | FFQTKDEVDNLLLKE | (SEQ ID NO: 27) | 7 |
| BDLF2 | AKAEERTAEMDDTMA | (SEQ ID NO: 28) | 3 |
| BDLF2 | GGMKRKQCRVDRLTD | (SEQ ID NO: 29) | 8 |
| BDLF3 | AHARDKAGAVMAMIL | (SEQ ID NO: 1) | 2 |
| BDLF3 | PTVPDERQPSLSYGL | (SEQ ID NO: 30) | 12 |
| BKRF2 | ASLNSPKNGSNQLVI | (SEQ ID NO: 2) | 4 |
| BILF2 | CNYSAGEEDDQYHAN | (SEQ ID NO: 8) | 20 |
| BILF2 | RPHRRPVSKRPTHKP | (SEQ ID NO: 9) | 23 |
| BSRF1 | BEPETFECPDRWRAE | (SEQ ID NO: 31) | 5 |
| BGLF1 | EITQEENRGEQRLGH | (SEQ ID NO: 10) | 21 |
| BGLF1 | VSFSKTRRAIRESRA | (SEQ ID NO: 7) | 18 |
| BALF1 | LIKASLRKDRYLYAE | (SEQ ID NO: 6) | 9 |
| BALF1 | YAVFTRDEKDLPLPA | (SEQ ID NO: 32) | 19 |
| BBRF3 | ELESEPRPRPSRTPS | (SEQ ID NO: 3) | 6 |
| BBRF3 | RSSTSSSSSRSTRRQ | (SEQ ID NO: 33) | 15 |
| BXRF1 | GALRARLDRPRPTAQ | (SEQ ID NO: 11) | 22 |
| BXRF1 | PRSARAGRAGGRKGQ | (SEQ ID NO: 34) | 11 |
| BORF1 | MKVQGSVDRRRLQRR | (SEQ ID NO: 35) | 10 |
| BORF1 | RGSEFTRDVRGLVEE | (SEQ ID NO: 36) | 14 |
| BLRF2 | QAMKKIEDKVRKSVD | (SEQ ID NO: 4) | 13 |
| BLRF2 | SRSRGREAKKVQISD | (SEQ ID NO: 5) | 16 |
| BMRF2 | TSGLERRRSIFCARG | (SEQ ID NO: 37) | 17 |

ELISA assay

The stock peptide-BSA conjugate was diluted 1/100 with DD $H_2O$ and 50 µl of the peptide-BSA conjugate were added to each well in 96 well microtiter plates (Flow Laboratories) and the plates were left overnight at 37° C. to dry. To block the wells 200 µl of a solution containing 5% BSA, 0.5M carbonate buffer pH 9.0 were added and left for 30 minutes at ambient temperature. The wells were then washed four times with 200 µl of 0.1% BSA-PBS/1% Tween. Human sera (diluted 1 in 100 in 5% BSA/2×PBS/1% Tween) were added and incubated at 21° C. for 1 h. The plates were then washed six times with 0.1% BSA/2×PBS/0.1% Tween and 100 µl of peroxidaselabelled anti-human IgM (Tago, µ fraction) (diluted 1/5000 in 5% BSA/2×PBS/0.1% Tween) were added and then the plates incubated at 37° C. for 30 minutes. The plates were again washed six times as above. The plates were given a rinse with distilled water (neutral pH), and substrate (100 µl of 1 mM ABTS (2,2-azino-bis(3-ethlybenzthiazoline-6-sulphonic acid) diammonium salt (Sigma, St. Louis, USA) in 100 mM phosphate-citrate buffer (pH 4.3) containing 0.004% (v/v) hydrogen peroxide) were added and the plates incubated at 37° C. for 30 minutes. Finally the plates were read at 410 nm.

Subjects and sera

Samples of sera (26) were obtained from patients with IM. These patients were diagnosed as having clinical symptoms of IM and were confirmed by immunofluoresence assays for IgM and IgG antibodies to VCA and by immunoblotting for antibodies to early antigens (EA) and absence of antibodies to EBV nuclear antigen 1 (EBNA1). Sera (14 were EBV seropositive and 8 EBV seronegative) were also obtained from healthy controls and their EBV status was determined by immunofluoresence assays to the EBV antigens. The normal controls were all negative for IgM antibodies to EBV. For the clinical trials, hundreds of samples of serum, from patients displaying IM-like symptoms, were collected.

Immunofluoresence assay for EBV antigens.

Anti-VCA titres were measured according to the method of Henle and Henle. (J Bacteriol. 91, 1248–1256).

Heterophil antibody assay

The Paul Bunnell test was used to measure heterophil antibody titres in serum.

Results and Discussion

Screening of EBV peptides

The 23 synthetic peptides were initially screened against 26 samples of sera from confirmed. IM patients, 8 EBV seronegative controls and 14 EBV seropositive controls. The results, presented in FIG. 1, illustrate that a number of peptides were reactive with IgM antibodies from IM patients while showing little reaction with the sera from either EBV seropositive or seronegative controls. Peptides #2, 4, 6, 13, 16 and 18 were selected for further studies.

Reaction of IM and normal sera with selected EBV peptides.

Figure 2:
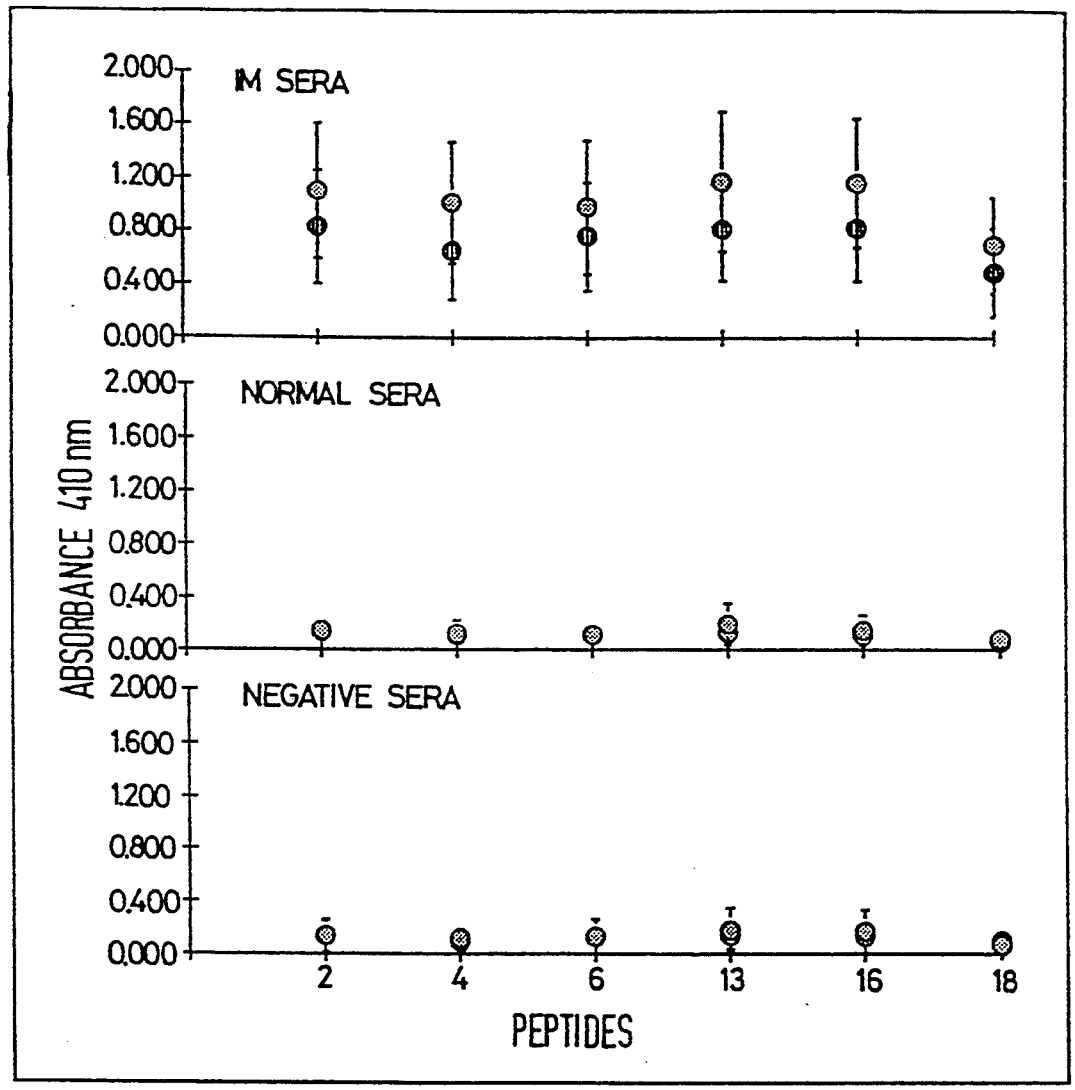
FIG. 2 is a graphic representation of a comparison of total Ig and IgM reactions with peptides of the invention.

Comparison of total Ig and IgM reactions with the peptides indicated that normal seropositive individuals lacked both IgM and IgG antibodies to these peptides (FIG. 2). However, it appeared that IM patients contained only IgM antibodies to these peptides. Measurement of IgG antibodies to the peptides, in both IM sera and sera from normal controls, confirmed the absence of these antibodies (results not shown).

These results indicated that measurement of either IgM or total Ig could be useful in identifying serum samples from IM patients.

Since only IgM antibodies to the peptides appear to be present in IM patients, there should not be a problem with rheumatoid factor or interference from IgG antibodies, both of which are usually a problem with indirect ELISA assays.

Clinical study

In order to ascertain the viability of using the peptides to identify cases of IM, sera were obtained from patients who showed clinical symptoms of IM. These sera were assayed by ELISA, using the 6 selected synthetic peptides, by immunofluoresence for the presence of IgM antibodies to VCA and for heterophil antibodies. Patients were considered to have IM if they were both heterophil positive (titres of 1/16 or higher) and IgM positive (titres of 1/40 or higher) by immunofluorescence or heterophil negative but with atypical monnuclear cells and IgM positive by immunofluoresence. The ELISA based IgM assay using the synthetic peptides was considered to be positive when a serum reacted with four or more of the peptides ($A^{410}$ of 0.40 or above). The results of the assays, obtained with all of the patients, are shown in Table 2.

TABLE 2

| Patient | Heterophil | ATLs (%) | ELISA (IgM) | IFA (IgM) |
|---|---|---|---|---|
| 1 | <10 | 0 | — | <10 |
| 2 | 64 | 13 | + | 160 |
| 3 | <10 | 0 | — | <10 |
| 4 | <10 | 0 | — | <10 |
| 5 | <10 | 0 | — | <10 |
| 6 | <10 | 0 | — | <10 |
| 7 | <10 | 0 | — | <10 |
| 8 | <10 | 0 | — | <10 |
| 9 | <10 | 0 | + | 160 |
| 10 | <10 | 0 | — | <10 |
| 11 | <10 | 0 | — | <10 |
| 12 | <10 | 0 | — | <10 |
| 13 | <10 | 0 | — | <10 |
| 14 | <10 | 0 | — | <10 |
| 15 | <10 | 0 | — | <10 |
| 16 | <10 | 0 | — | <10 |
| 17 | <10 | 0 | — | <10 |
| 18 | <10 | 0 | — | <10 |
| 19 | <10 | 0 | — | <10 |
| 20 | <10 | 0 | — | <10 |
| 21 | <10 | 0 | — | <10 |
| 22 | <10 | 15 | + | 160 |
| 23 | <10 | 0 | — | <10 |
| 24 | 256 | 21 | + | 160 |
| 25 | <10 | 0 | — | <10 |
| 26 | <10 | 0 | — | <10 |
| 27 | <10 | 0 | — | <10 |
| 28 | <10 | 0 | — | <10 |
| 29 | <10 | 14 | — | <10 |
| 30 | <10 | 3 | — | <10 |
| 31 | <10 | 0 | — | <10 |
| 32 | <10 | 0 | — | <10 |
| 33 | 10 | 0 | — | 160 |
| 34 | <10 | 0 | — | <10 |
| 35 | <10 | 0 | — | <10 |
| 36 | <10 | 0 | — | <10 |
| 37 | <10 | 0 | — | <10 |
| 38 | <10 | 0 | — | <10 |
| 39 | <10 | 0 | — | <10 |
| 40 | <10 | 24 | — | <10 |
| 41 | <10 | 0 | — | <10 |
| 42 | <10 | 0 | — | <10 |
| 43 | <10 | 0 | — | <10 |
| 44 | <10 | 16 | — | <10 |
| 45 | <10 | 0 | — | <10 |
| 46 | 64 | 24 | + | 360 |
| 47 | <10 | 0 | — | <10 |
| 48 | 16 | 0 | — | <10 |
| 49 | <10 | 2 | — | <10 |
| 50 | <10 | 0 | — | <10 |
| 51 | <10 | 0 | — | <10 |
| 52 | <10 | 0 | — | <10 |
| 53 | <10 | 3 | — | 10 |
| 54 | <10 | 0 | — | <10 |
| 55 | <10 | 0 | — | <10 |
| 56 | 64 | 65 | — | 320 |
| 57 | <10 | 0 | — | <10 |
| 58 | <10 | 0 | — | <10 |
| 59 | <10 | 0 | — | <10 |
| 60 | <10 | 0 | — | <10 |
| 61 | <10 | 0 | — | <10 |
| 62 | <10 | 1 | — | <10 |
| 63 | 16 | 0 | — | <10 |
| 64 | 256 | 39 | + | 160 |
| 65 | <10 | 9 | — | <10 |
| 66 | <10 | 0 | — | <10 |
| 67 | <10 | 0 | — | <10 |
| 68 | <10 | 0 | — | <10 |
| 69 | <10 | 0 | — | <10 |
| 70 | <10 | 0 | — | <10 |
| 71 | <10 | 0 | + | <10 |
| 72 | 256 | 23 | + | 320 |

TABLE 2-continued

| Patient | Heterophil | ATLs (%) | ELISA (IgM) | IFA (IgM) |
|---|---|---|---|---|
| 73 | <10 | 0 | — | <10 |
| 74 | <10 | 0 | — | <10 |
| 75 | <10 | 9 | + | 40 |
| 76 | <10 | 0 | — | <10 |
| 77 | <10 | 0 | — | <10 |
| 78 | <10 | 0 | — | <10 |
| 79 | <10 | 0 | — | <10 |
| 80 | <10 | 0 | — | <10 |
| 81 | <10 | 0 | — | <10 |
| 82 | <10 | 0 | — | <10 |
| 83 | <10 | 0 | — | <10 |
| 84 | <10 | 0 | — | <10 |
| 85 | <10 | 0 | — | <10 |
| 86 | 64 | 19 | + | 160 |
| 87 | <10 | 0 | — | <10 |
| 88 | 64 | 4 | + | 160 |
| 89 | <10 | 0 | — | <10 |
| 90 | <10 | 0 | — | <10 |
| 91 | 64 | 45 | + | 160 |
| 92 | <10 | 0 | — | <10 |
| 93 | <10 | 0 | — | <10 |
| 94 | <10 | 0 | — | <10 |
| 95 | 256 | 32 | + | 160 |
| 96 | <10 | 0 | — | <10 |
| 97 | <10 | 0 | — | <10 |
| 98 | <10 | 0 | — | <10 |
| 99 | <10 | 2 | — | <10 |
| 100 | <10 | 3 | — | <10 |
| 101 | <10 | 0 | — | <10 |
| 102 | <10 | 0 | — | <10 |
| 103 | <10 | 0 | — | <10 |
| 104 | 16 | 30 | + | 160 |

The results of the statistical analysis of the correlation between the three assays systems are presented in Table 3.

TABLE 3

| CORRELATIONS AND POLYCHORIC TEST STATISTICS | | | |
|---|---|---|---|
| | ELISA | IF (IgM) | HETEROPHIL |
| ELISA | 1.000 | 0.988 | 0.901 |
| IF (IgM) | | 1.000 | 0.964 |
| HETEROPHIL | | | 1.000 |

| ASYMPTOTIC VARIANCES OF ESTIMATED CORRELATIONS | |
|---|---|
| ELISA-IF (IgM) = | 0.00020 |
| ELISA-HETEROPHIL = | 0.00407 |
| IF (IgM)-HETEROPHIL = | 0.00094 |

The results obtained from the statistical analysis demonstrate a 96% correlation between the IF-IgM assay and the heterophil antibody assay which better the reported data. However, the correlation between the ELISA assay and IF-IgM was 99% indicating that this assay was more accurate at predicting patients with IM. There was one serum which was ELISA positive but IF-IgM negative and it is possible that this patient may have not as yet developed a high enough titre of IgM antibodies to be detected by the IF-IgM test. Two sera samples were positive by IF-IgM and negative by the ELISA assay. Peptides #2, 4 and 6 were selected for further clinical trials, whereby 510 samples of serum, from patients displaying IM-like symptoms, were assayed for heterophil antibody using the Paul Bunnell test and for the presence of IgM antibodies to EBV by immunofluoresence as described above. These results were then correlated with the results obtained using the ELISA assay with the three synthetic EBV peptides and with the Monolert assay as marketed by Johnson and Johnson. The statistical analysis of these results are shown below.

peptides were prepared and assayed by ELISA using a pooled IM positive sera and a pooled normal sera.

|  | TEST OF MODEL | | | TEST OF ZERO CORR. | |
|---|---|---|---|---|---|
|  | Correlat. | Chi-squ.DF | P-VALUE | CHI-SQU. | P-VALUE |
| CORRELATIONS AND TEST STATISTICS (PC=POLYCHORIC) | | | | | |
| IFA VS. PB | .868 (PC) | .000 0 | 1.000 | 889.303 | .000 |
| ELISA VS. PB | .882 (PC) | .000 0 | 1.000 | 969.017 | .000 |
| ELISA VS. IFA | .897 (PC) | .000 0 | 1.000 | 1073.819 | .000 |
| MONO VS. PB | .718 (PC) | .000 0 | 1.000 | 413.573 | .000 |
| MONO VS. IFA | .595 (PC) | .000 0 | 1.000 | 238.506 | .000 |
| MONO VS. ELISA | .614 (PC) | .000 0 | 1.000 | 259.295 | .000 |
|  | PB | IFA | ELISA | MONO | |
| ESTIMATED CORRELATION MATRIX | | | | | |
| PB | 1.000 | | | | |
| IFA | 0.868 | 1.000 | | | |
| ELISA | 0.882 | 0.897 | 1.000 | | |
| MONO | 0.718 | 0.595 | 0.614 | 1.000 | |

PB - Paul Bunnell
IFA - Immunofluoresence assay for EBV-specific IgM
ELISA - ELISA assay using the synthetic EBV peptides of the invention
MONO - Monolert assay as marketed by Johnson and Johnson

| ORIGINAL 15-mers PEPTIDES | |
|---|---|
| #4 ASLNSFKNGSNQLVI | (SEQ ID NO: 2) |
| #2 AHARDKAGAVMAMIL | (SEQ ID NO: 1) |
| #6 ELESEPRPRPSRTPS | (SEQ ID NO: 3) |

| | SYNTHETIC OVERLAPPING PEPTIDES | | |
|---|---|---|---|
| PEPTIDE | | POSITIVE SERA | NEGATIVE SERA |
| ASLNSPKNGSNQLVI (SEQ ID NO: 2) | | | |
| ASLNSP | (SEQ ID NO: 38) | 0.287 | 0.110 |
| **NSPKNG | (SEQ ID NO: 12) | 0.555 | 0.143 |
| **KNGSNQ | (SEQ ID NO: 13) | 0.537 | 0.141 |
| **SNQLVI | (SEQ ID NO: 14) | 0.437 | 0.133 |
| AHARDKAGAVMAMIL (SEQ. ID NO: 1) | | | |
| **AHARDK | (SEQ ID NO: 15) | 0.639 | 0.215 |
| **RDKAGA | (SEQ ID NO: 16) | 0.496 | 0.122 |
| AGAVMA | (SEQ ID NO: 39) | 0.324 | 0.099 |
| **VMAMIL | (SEQ ID NO: 17) | 0.505 | 0.170 |
| ELESEPRPRPSRTPS (SEQ ID NO: 3) | | | |
| ELESEP | (SEQ ID NO: 40) | 0.150 | 0.063 |
| **SEPRPR | (SEQ ID NO: 18) | 0.623 | 0.228 |
| RPRPSR | (SEQ ID NO: 41) | 0.407 | 0.131 |
| **PSRTPS | (SEQ ID NO: 19) | 0.546 | 0.185 |

**-INDICATES THE PEPTIDES CONTAINING B-CELL EPITOPES.

These results show a much higher correlation between the synthetic peptides of the invention and the IFA assay than did the PB test or the Monolert assay.

Rather than use three independent peptides in the assay system, longer peptides containing combinations of B-cell epitopes (i.e. the epitopes to which the antibodies bind) from each of the 15 amino acid peptides were constructed. To define the B-cell epitopes in each of the three peptides overlapping 6 amino acid synthetic Having defined the B-cell epitopes contained within the original 15 aa peptides, different combinations of these epitopes were used in the synthesis of larger synthetic peptides. Examples of some of these combinations are shown below:

| EPITOPE COMBINATIONS: | | |
|---|---|---|
| PEPTIDE A. | NSPKNGSNQAHARDKSEPRPR | (SEQ ID NO: 20) |
| PEPTIDE B. | NSPKNGSNQRDKAGASEPRPR | (SEQ ID NO: 21) |
| PEPTIDE C. | NSPKNGSNQSEPRPRKNGSNQ | (SEQ ID NO: 22) |
| PEPTIDE D. | NSPKNGSNQLVISEPRPRPSRTPS | (SEQ ID NO: 23) |
| PEPTIDE E. | NSPKNGSNQLVIPSRTPS | (SEQ ID NO: 24) |
| PEPTIDE F. | NSPKNGSNQAHARDKAGASEPRPR | (SEQ ID NO: 25) |

These 6 peptides were then tested for their reaction with sera from known IM patients and with sera from normal controls. The sera were all well characterized for the presence/absence of IgM antibodies to EBV by immunofluoresence. The results of that testing are presented in Table 4.

TABLE 4

| Peptide | A* | B** | IM1 | IM2 | IM3 | IM4 | IM5 | NOR1 | NOR2 | NOR3 | NOR4 | NOR5 | NOR6 |
|---|---|---|---|---|---|---|---|---|---|---|---|---|---|
| A | 1.58 | 0.25 | 1.34 | 1.34 | 1.34 | 1.52 | 1.53 | 0.63 | 0.16 | 0.31 | 0.13 | 0.25 | 0.47 |
| B | 1.64 | 0.19 | 1.20 | 1.35 | 1.24 | 1.63 | 1.15 | 0.48 | 0.19 | 0.25 | 0.11 | 0.20 | 0.38 |
| C | 1.04 | 0.12 | 0.81 | 1.11 | 0.93 | 1.47 | 0.85 | 0.21 | 0.15 | 0.32 | 0.12 | 0.14 | 0.24 |
| D | 1.31 | 0.17 | 0.97 | 1.14 | 1.05 | 1.49 | 0.87 | 0.36 | 0.16 | 0.24 | 0.12 | 0.14 | 0.21 |
| E | 1.20 | 0.12 | 0.64 | 1.07 | 0.88 | 1.46 | 0.67 | 0.25 | 0.15 | 0.17 | 0.11 | 0.13 | 0.21 |
| F | 1.55 | 0.09 | 1.15 | 1.22 | 1.19 | 1.60 | 1.12 | 0.37 | 0.21 | 0.39 | 0.15 | 0.24 | 0.37 |

*Pooled control IM serum
**Pooled control normal serum
IM Infectious mononucleosis
NOR Normal These results demonstrate that any of these epitope combinations could be used to identify serum from IM patients. However some of the peptides gave reasonably strong reactions with sera from normal individuals (peptides A, B and F in particular). Of those peptides which had low reactions with the normal sera peptide E gave the lowest values and so was chosen for further studies.

Peptide E was assayed with a larger contingent of sera from patients with IM and normal controls. Control wells, containing only BSA, were also included in the assay to check for sera which may react with the carrier protein. The results of that assay are presented in Table 5.

TABLE 5

ELISA ASSAY OF PEPTIDE E.

| SERA | DIAGNOSIS | PEPTIDE WELL | BLANK WELL (BSA) |
|---|---|---|---|
| A | Positive control | 0.993 | 0.066 |
| B | Negative control | 0.116 | 0.068 |
| 1 | IM | 1.050 | 0.077 |
| 2 | IM | 1.133 | 0.072 |
| 3 | IM | 0.689 | 0.056 |
| 4 | IM | 0.780 | 0.064 |
| 5 | IM | 0.852 | 0.085 |
| 6 | IM | 0.598 | 0.051 |
| 7 | IM | 0.813 | 0.053 |
| 8 | IM | 0.953 | 0.062 |
| 9 | IM | 1.093 | 0.051 |
| 10 | IM | 0.739 | 0.054 |
| 11 | IM | 1.128 | 0.043 |
| 12 | IM | 0.933 | 0.056 |
| 13 | IM | 0.795 | 0.058 |
| 14 | IM | 0.556 | 0.051 |
| 15 | IM | 0.717 | 0.047 |
| 16 | IM | 1.454 | 0.065 |
| 17 | Normal | 0.101 | 0.049 |
| 18 | Normal | 0.187 | 0.055 |
| 19 | Normal | 0.098 | 0.051 |
| 20 | Normal | 0.072 | 0.052 |
| 21 | Normal | 0.149 | 0.045 |
| 22 | Normal | 0.061 | 0.050 |
| 23 | Normal | 0.073 | 0.044 |
| 24 | Normal | 0.080 | 0.045 |
| 25 | Normal | 0.120 | 0.047 |
| 26 | Normal | 0.159 | 0.052 |
| 27 | Normal | 0.142 | 0.057 |
| 28 | Normal | 0.054 | 0.046 |
| 29 | Normal | 0.270 | 0.076 |
| 30 | Normal | 0.336 | 0.045 |
| 31 | Normal | 0.280 | 0.051 |
| 32 | Normal | 0.337 | 0.041 |
| 33 | Normal | 0.136 | 0.042 |

These results demonstrate that peptide E could be used to reliably detect cases of IM while showing little reaction with sera from normal individuals.

The clinical and other data obtained indicates that the ELISA assay using the peptides of the present invention is a specific and reliable test for the diagnosis of infectious mononucleosis and related diseases. The present invention should also find use in the treatment of such diseases.

Those skilled in the art will appreciate that the above embodiments are given by way of exemplification of the invention only, and that changes may be made to the details set out therein without departing from the scope of the invention as defined in the following claims.

We claim:

1. A Synthetic peptide consisting of an amino acid sequence wherein an antigenic epitope of Epstein-Barr virus (EBV) is contained, said amino acid sequence selected from the group consisting of AHARDKAGAVMAMIL (SEQ ID NO: 1), ASLNSPKNGSNQLVI (SEQ ID NO: 2), ELESEPRPRPSRTPS (SEQ ID NO: 3), QAMKKIEDKVRKSVD (SEQ ID NO: 4), LIKASLRKDRKLYAE (SEQ ID NO: 6), VSFSKTRRAIRESRA (SEQ ID NO: 7), CNYSAGEEDDQYHAN (SEQ ID NO: 8), RPHRRPVSKRPTHKP (SEQ ID NO: 9), EITQEENRGEQRLGH (SEQ ID NO: 10), GALRARLDRPRPTAQ (SEQ ID NO: 11), SRSRGREAKKVQISD (SEQ ID NO: 5), NSPKNG (SEQ ID NO: 12), KNGSNQ (SEQ ID NO: 13), SNQLVI (SEQ ID NO: 14), AHARDK (SEQ ID NO: 15), RDKAGA (SEQ ID NO: 16), VMAMIL (SEQ ID NO: 17), SEPRPR (SEQ ID NO: 18), PSRTPS (SEQ ID NO: 19), NSPKNGSNQAHARDKSEPRPR (SEQ ID NO: 20), NSPKNGSNQRDKAGASEPRPR (SEQ ID NO: 21), NSPKNGSNQSEPRPRKNGSNQ (SEQ ID NO: 22), NSPKNGSNQLVISEPRPRPSRTPS (SEQ ID NO: 23), NSPKNGSNQLVIPSRTPS (SEQ ID NO: 24), and NSPKNGSNQAHARDKAGASEPRPR (SEQ ID NO: 25).

2. A peptide as defined in claim 1 wherein said amino acid sequence consists of the sequence AHARDKAGAVMAMIL (SEQ ID NO: 1).

3. A peptide as defined in claim 1 wherein said amino acid sequence consists of the sequence ASLNSPKNGSNQLVI (SEQ ID NO: 2).

4. A peptide as defined in claim 1 wherein said amino acid sequence consists of the sequence ELESEPRPRPSRTPS (SEQ ID NO: 3).

5. A peptide as defined in claim 1 wherein said amino acid sequence consists of the sequence QAMKKIEDKVRKSVD (SEQ ID NO: 4).

6. A peptide as defined in claim 1 wherein said amino acid sequence consists of the sequence LIKASLRKDRKLYAE (SEQ ID NO: 6).

7. A peptide as defined in claim 1 wherein said amino acid sequence consists of the sequence VSFSKTRRAIRESRA (SEQ ID NO: 7).

8. A peptide as defined in claim 1 wherein said amino acid sequence consists of the sequence CNYSAGEEDDQYHAN (SEQ ID NO: 8).

9. A peptide as defined in claim 1 wherein said amino acid sequence consists of the sequence RPHRRPVSKRPTHKP (SEQ ID NO: 9).

10. A peptide as defined in claim 1 wherein said amino acid sequence consists of the sequence EITQEENRGEQRLGH (SEQ ID NO: 10).

11. A peptide as defined in claim 1 wherein said amino acid sequence consists of the sequence GALRARLDRPRPTAQ (SEQ ID NO: 11).

12. A peptide as defined in claim 1 wherein said amino acid sequence consists of the sequence SRSRGREAKKVQISD (SEQ ID NO: 5).

13. A peptide as defined in claim 1 wherein said amino acid sequence consists of the sequence NSPKNG (SEQ ID NO: 12).

14. A peptide as defined in claim 1 wherein said amino acid sequence consists of the sequence KNGSNQ (SEQ ID NO: 13).

15. A peptide as defined in claim 1 wherein said amino acid sequence consists of the sequence SNQLVI (SEQ ID NO: 14).

16. A peptide as defined in claim 1 wherein said amino acid sequence consists of the sequence AHARDK (SEQ ID NO: 15).

17. A peptide as defined in claim 1 wherein said amino acid sequence consists of the sequence RDKAGA (SEQ ID NO: 16).

18. A peptide as defined in claim 1 wherein said amino acid sequence consists of the sequence VMAMIL (SEQ ID NO: 17).

19. A peptide as defined in claim 1 wherein said amino acid sequence consists of the sequence SEPRPR (SEQ ID NO: 18).

20. A peptide as defined in claim 1 where(n said amino acid sequence consists of the sequence PSRTPS (SEQ ID NO: 19).

21. A peptide as defined in claim 1 wherein said amino acid sequence consists of the sequence NSPKNGSNQAHARDKSEPRPR (SEQ ID NO: 20).

22. A peptide as defined in claim 1 wherein said amino acid sequence consists of the sequence NSPKNGSNQRDKAGASEPRPR (SEQ ID NO: 21).

23. A peptide as defined in claim 1 wherein said amino acid sequence consists of the sequence NSPKNGSNQSEPRPRKNGSNQ (SEQ ID NO: 22).

24. A peptide as defined in claim 1 wherein said amino acid sequence consists of the sequence NSPKNGSNQLVISEPRPRPSRTPS (SEQ ID NO: 23).

25. A peptide as defined in claim 1 wherein said amino acid sequence consists of the sequence NSPKNGSNQLVIPSRTPS (SEQ ID NO: 24).

26. A peptide as defined in claim 1 wherein said amino acid sequence consists of the sequence NSPKNGSNQAHARDKAGASEPRPR (SEQ ID NO: 25).

27. A method of diagnosis of infectious mononucleosis comprising assaying serum by immunoassay from a patient suspected of having infectious mononucleosis with at least one peptide as defined in claim 1 and determining the presence of an immunoreaction between said peptide and anti-EBV antibodies.

28. A kit for use in the diagnosis of infectious mononucleosis (IM) comprising:
  (a) at least one peptide as defined in claim 1; and
  (b) a means for indicating the presence of an immunoreaction between said peptide and anti-EBV antibodies.

* * * * *

SEQUENCE LISTING ( 1 ) GENERAL INFORMATION:

( i i i ) NUMBER OF SEQUENCES: 41

( 2 ) INFORMATION FOR SEQ ID NO:1:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:1:

```
    Ala  His  Ala  Arg  Asp  Lys  Ala  Gly  Ala  Val  Met  Ala  Met  Ile  Leu
    1              5                        10                            15
```

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:2:

```
    Ala  Ser  Leu  Asn  Ser  Pro  Lys  Asn  Gly  Ser  Asn  Gln  Leu  Val  Ile
    1              5                        10                            15
```

( 2 ) INFORMATION FOR SEQ ID NO:3:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:3:

```
    Glu  Leu  Glu  Ser  Glu  Pro  Arg  Pro  Arg  Pro  Ser  Arg  Thr  Pro  Ser
    1              5                        10                            15
```

( 2 ) INFORMATION FOR SEQ ID NO:4:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:4:

```
    Gln  Ala  Met  Lys  Lys  Ile  Glu  Asp  Lys  Val  Arg  Lys  Ser  Val  Asp
    1              5                        10                            15
```

( 2 ) INFORMATION FOR SEQ ID NO:5:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:5:

Ser Arg Ser Arg Gly Arg Glu Ala Lys Lys Val Gln Ile Ser Asp
1               5                   10                  15

( 2 ) INFORMATION FOR SEQ ID NO:6:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:6:

Leu Ile Lys Ala Ser Leu Arg Lys Asp Arg Lys Leu Tyr Ala Glu
1               5                   10                  15

( 2 ) INFORMATION FOR SEQ ID NO:7:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:7:

Val Ser Phe Ser Lys Thr Arg Arg Ala Ile Arg Glu Ser Arg Ala
1               5                   10                  15

( 2 ) INFORMATION FOR SEQ ID NO:8:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:8:

Cys Asn Tyr Ser Ala Gly Glu Glu Asp Asp Gln Tyr His Ala Asn
1               5                   10                  15

( 2 ) INFORMATION FOR SEQ ID NO:9:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO (v) FRAGMENT TYPE: N-terminal (xi) SEQUENCE DESCRIPTION: SEQ ID NO:9:

Arg Pro His Arg Arg Pro Val Ser Lys Arg Pro Thr His Lys Pro
1               5                   10                  15

(2) INFORMATION FOR SEQ ID NO:10:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:10:

Glu Ile Thr Gln Glu Glu Asn Arg Gly Glu Gln Arg Leu Gly His
1               5                   10                  15

(2) INFORMATION FOR SEQ ID NO:11:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:11:

Gly Ala Leu Arg Ala Arg Leu Asp Arg Pro Arg Pro Thr Ala Gln
1               5                   10                  15

(2) INFORMATION FOR SEQ ID NO:12:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:12:

Asn Ser Pro Lys Asn Gly
1               5

(2) INFORMATION FOR SEQ ID NO:13:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:13:

```
Lys Asn Gly Ser Asn Gln
1               5
```

(2) INFORMATION FOR SEQ ID NO:14:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:14:

```
Ser Asn Gln Leu Val Ile
1               5
```

(2) INFORMATION FOR SEQ ID NO:15:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:15:

```
Ala His Ala Arg Asp Lys
1               5
```

(2) INFORMATION FOR SEQ ID NO:16:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:16:

```
Arg Asp Lys Ala Gly Ala
1               5
```

(2) INFORMATION FOR SEQ ID NO:17:

(i) SEQUENCE CHARACTERISTICS:
        (A) LENGTH: 6 amino acids
        (B) TYPE: amino acid
        (D) TOPOLOGY: linear (ii) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:17:

```
Val Met Ala Met Ile Leu
1               5
```

( 2 ) INFORMATION FOR SEQ ID NO:18:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:18:

```
Ser Glu Pro Arg Pro Arg
1               5
```

( 2 ) INFORMATION FOR SEQ ID NO:19:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:19:

```
Pro Ser Arg Thr Pro Ser
1               5
```

( 2 ) INFORMATION FOR SEQ ID NO:20:

( i ) SEQUENCE CHARACTERISTICS:
    ( A ) LENGTH: 21 amino acids
    ( B ) TYPE: amino acid
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:20:

```
Asn Ser Pro Lys Asn Gly Ser Asn Gln Ala His Ala Arg Asp Lys Ser
1               5                   10                  15
Glu Pro Arg Pro Arg
            20
```

( 2 ) INFORMATION FOR SEQ ID NO:21:

( i ) SEQUENCE CHARACTERISTICS:
    ( A ) LENGTH: 21 amino acids (B) TYPE: amino acid
(D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:21:

```
Asn  Ser  Pro  Lys  Asn  Gly  Ser  Asn  Gln  Arg  Asp  Lys  Ala  Gly  Ala  Ser
1                  5                        10                       15

Glu  Pro  Arg  Pro  Arg
               20
```

(2) INFORMATION FOR SEQ ID NO:22:

(i) SEQUENCE CHARACTERISTICS:
(A) LENGTH: 21 amino acids
(B) TYPE: amino acid
(D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:22:

```
Asn  Ser  Pro  Lys  Asn  Gly  Ser  Asn  Gln  Ser  Glu  Pro  Arg  Pro  Arg  Lys
1                  5                        10                       15

Asn  Gly  Ser  Asn  Gln
               20
```

(2) INFORMATION FOR SEQ ID NO:23:

(i) SEQUENCE CHARACTERISTICS:
(A) LENGTH: 24 amino acids
(B) TYPE: amino acid
(D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:23:

```
Asn  Ser  Pro  Lys  Asn  Gly  Ser  Asn  Gln  Leu  Val  Ile  Ser  Glu  Pro  Arg
1                  5                        10                       15

Pro  Arg  Pro  Ser  Arg  Thr  Pro  Ser
               20
```

(2) INFORMATION FOR SEQ ID NO:24:

(i) SEQUENCE CHARACTERISTICS:
(A) LENGTH: 18 amino acids
(B) TYPE: amino acid
(D) TOPOLOGY: linear (ii) MOLECULE TYPE: peptide (iii) HYPOTHETICAL: NO (iv) ANTI-SENSE: NO (v) FRAGMENT TYPE: N-terminal ( x i ) SEQUENCE DESCRIPTION: SEQ ID NO:24:

Asn Ser Pro Lys Asn Gly Ser Asn Gln Leu Val Ile Pro Ser Arg Thr
1               5                   10                  15

Pro Ser ( 2 ) INFORMATION FOR SEQ ID NO:25:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:25:

Asn Ser Pro Lys Asn Gly Ser Asn Gln Ala His Ala Arg Asp Lys Ala
1               5                   10                  15

Gly Ala Ser Glu Pro Arg Pro Arg
                20

( 2 ) INFORMATION FOR SEQ ID NO:26:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:26:

Ala Glu Asn Gln Asp Pro Glu Ala Lys Asp His Val Asn Ser Leu
1               5                   10                  15

( 2 ) INFORMATION FOR SEQ ID NO:27:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:27:

Phe Phe Gln Thr Lys Asp Glu Val Asp Asn Leu Leu Leu Lys Glu
1               5                   10                  15

( 2 ) INFORMATION FOR SEQ ID NO:28:

( i ) SEQUENCE CHARACTERISTICS:
        ( A ) LENGTH: 15 amino acids
        ( B ) TYPE: amino acid
        ( D ) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:28:

```
Ala  Lys  Ala  Glu  Glu  Arg  Thr  Ala  Glu  Met  Asp  Asp  Thr  Met  Ala
1                 5                        10                        15
```

(2) INFORMATION FOR SEQ ID NO:29:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:29:

```
Gly  Gly  Met  Lys  Arg  Lys  Gln  Cys  Arg  Val  Asp  Arg  Leu  Thr  Asp
1                 5                        10                        15
```

(2) INFORMATION FOR SEQ ID NO:30:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:30:

```
Pro  Thr  Val  Pro  Asp  Glu  Arg  Gln  Pro  Ser  Leu  Ser  Tyr  Gly  Leu
1                 5                        10                        15
```

(2) INFORMATION FOR SEQ ID NO:31:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:31:

```
Glu  Glu  Pro  Glu  Thr  Phe  Glu  Cys  Pro  Asp  Arg  Trp  Arg  Ala  Glu
1                 5                        10                        15
```

(2) INFORMATION FOR SEQ ID NO:32:

(i) SEQUENCE CHARACTERISTICS:
        (A) LENGTH: 15 amino acids
        (B) TYPE: amino acid ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:32:

```
Tyr Ala Val Phe Thr Arg Asp Glu Lys Asp Leu Pro Leu Pro Ala
1               5                   10                  15
```

( 2 ) INFORMATION FOR SEQ ID NO:33:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:33:

```
Arg Ser Ser Thr Ser Ser Ser Ser Arg Ser Thr Arg Arg Gln
1               5                   10                  15
```

( 2 ) INFORMATION FOR SEQ ID NO:34:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:34:

```
Pro Arg Ser Ala Arg Ala Gly Arg Ala Gly Gly Arg Lys Gly Gln
1               5                   10                  15
```

( 2 ) INFORMATION FOR SEQ ID NO:35:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:35:

```
Met Lys Val Gln Gly Ser Val Asp Arg Arg Arg Leu Gln Arg Arg
1               5                   10                  15
```

( 2 ) INFORMATION FOR SEQ ID NO:36:

( i ) SEQUENCE CHARACTERISTICS:

(A) LENGTH: 15 amino acids
(B) TYPE: amino acid
(D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:36:

```
Arg Gly Ser Glu Phe Thr Arg Asp Val Arg Gly Leu Val Glu Glu
  1               5                  10                  15
```

(2) INFORMATION FOR SEQ ID NO:37:

(i) SEQUENCE CHARACTERISTICS:
(A) LENGTH: 15 amino acids
(B) TYPE: amino acid
(D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:37:

```
Thr Ser Gly Leu Glu Arg Arg Arg Ser Ile Phe Cys Ala Arg Gly
  1               5                  10                  15
```

(2) INFORMATION FOR SEQ ID NO:38:

(i) SEQUENCE CHARACTERISTICS:
(A) LENGTH: 6 amino acids
(B) TYPE: amino acid
(D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:38:

```
Ala Ser Leu Asn Ser Pro
  1               5
```

(2) INFORMATION FOR SEQ ID NO:39:

(i) SEQUENCE CHARACTERISTICS:
(A) LENGTH: 6 amino acids
(B) TYPE: amino acid
(D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:39:

```
Ala Gly Ala Val Met Ala
  1               5
```

(2) INFORMATION FOR SEQ ID NO:40:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:40:

Glu  Leu  Glu  Ser  Glu  Pro
1                    5

( 2 ) INFORMATION FOR SEQ ID NO:41:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:41:

Arg  Pro  Arg  Pro  Ser  Arg
1                    5